United States Patent
Kubey et al.

(10) Patent No.: US 7,956,756 B2
(45) Date of Patent: Jun. 7, 2011

(54) REM-SLEEP DIRECTED VISUAL ALARM SYSTEM AND METHOD

(76) Inventors: Alan Kubey, Davis, CA (US); Andrew Davidson, Palo Alto, CA (US)

( * ) Notice: Subject to any disclaimer, the term of this patent is extended or adjusted under 35 U.S.C. 154(b) by 346 days.

(21) Appl. No.: 12/389,362

(22) Filed: Feb. 19, 2009

(65) Prior Publication Data

US 2009/0207028 A1 Aug. 20, 2009

Related U.S. Application Data

(60) Provisional application No. 61/066,302, filed on Feb. 19, 2008.

(51) Int. Cl.
*G08B 23/00* (2006.01)
*A61B 5/08* (2006.01)

(52) U.S. Cl. .................. 340/575; 340/573.1; 600/595

(58) Field of Classification Search ............... 340/573.1, 340/575, 576; 600/529, 544, 545, 558, 595; 351/206, 209, 221
See application file for complete search history.

(56) References Cited

U.S. PATENT DOCUMENTS

| | | | |
|---|---|---|---|
| 4,858,609 A | 8/1989 | Cole | |
| 4,863,259 A | 9/1989 | Schneider et al. | |
| 5,008,865 A | 4/1991 | Shaffer et al. | |
| 5,137,345 A * | 8/1992 | Waldorf et al. | 351/206 |
| 5,507,716 A | 4/1996 | LaBerge et al. | |
| 6,350,275 B1 | 2/2002 | Vreman et al. | |
| 6,669,627 B1 | 12/2003 | Campbell et al. | |
| 6,928,031 B1 | 8/2005 | Kanevsky et al. | |
| 7,248,915 B2 | 7/2007 | Ronnholm | |
| 7,371,220 B1 * | 5/2008 | Koh et al. | 600/529 |
| 7,774,052 B2 * | 8/2010 | Burton et al. | 600/544 |
| 2008/0074618 A1 * | 3/2008 | Qi | 351/221 |
| 2009/0149770 A1 * | 6/2009 | Sing | 600/544 |

OTHER PUBLICATIONS

Harper, Hoppenbrouwers and Ross, A New Technique for Long-Term Recording of Eye Movement in Infants, Electroencephalography and Clinical Neuophysiology, 40 (1976) 109-112, Elsevier Scientific Publishing Company, Amsterdam—Printed in The Netherlands.

* cited by examiner

*Primary Examiner* — Van T. Trieu
(74) *Attorney, Agent, or Firm* — Temmerman Law Office; Mathew J. Temmerman

(57) ABSTRACT

The present apparatus and method for using the same detects Rapid Eye Movement (REM) in a sleeping mammal and awakens the mammal after the cessation of a specific episode of REM. The system comprises an alarm setting unit for setting a predetermined wakeup time, a data collection unit for collecting physiological data from the mammal over time, a processing unit for determining the occurrence and cessation of REM and for providing a stimulation signal for awakening the mammal within a prescribed window of time before the predetermined wakeup time and after the cessation of REM and after the mammal's nadir in body temperature with respect to time.

20 Claims, 5 Drawing Sheets

REM-SLEEP DIRECTED VISUAL ALARM SYSTEM AND METHOD

RELATED APPLICATIONS

This application is related to and claims priority from previously filed U.S. provisional patent application Ser. No. 61/066,302, filed Feb. 19, 2008, which is incorporated by reference herein as if set out in full.

BACKGROUND OF THE INVENTION

1. Field of the Invention

The present invention relates to sleep optimization, and more particularly to providing a system for optimizing an individual's time spent sleeping, for providing a uniquely timed wake up alert to minimize the pitfalls of sleep inertia, to leave the individual feeling energized, and to entrain the individual's circadian rhythm.

2. General Background

The physiological phenomenon of human sleep is heterogeneous in nature, and its great variation is influenced heavily by factors outside the body. As part of understanding sleep and what affects it, a great deal of research has generally agreed that sleep can be broken down into two broad types: Rapid Eye Movement (REM) and Non-Rapid Eye Movement (NREM). NREM is subdivided into light sleep, which consists of Stage 1 and Stage 2 sleep, and slow wave sleep (SWS, also known as "deep sleep" or "delta sleep"), which consists of Stage 3 and Stage 4 (some researchers no longer divide SWS into Stage 3 and Stage 4, and instead treat it as a single stage). As the above named stages imply, NREM sleep comprises four successively deeper stages of sleep—Stages 1 through 4. While sleeping, humans cycle through the above stages, as shown best in FIG. 1. A typical sleep cycle begins with the transition from waking to Stage 1 sleep and then progresses through Stage 2, Stage 3, and finally Stage 4 before returning back through Stage 3 to Stage 2. Rather than progressing all the way back to Stage 1 sleep, at this time the typical sleep cycle enters REM sleep (sometimes with a transitory pass through Stage 1 sleep). Stage 4 can be seen in FIG. 1 just above the 1-hour mark, and the transition back to the lighter stages is seen immediately thereafter. Upon the conclusion of REM sleep, the typical sleep cycle progresses back to Stage 2 (also sometimes with a transitory pass through Stage 1) and on to Stage 3 and Stage 4 and then back through Stage 3 and Stage 2 at which time the cycle again enters REM sleep (again, possibly with a transitory pass through Stage 1) and repeats. While there is significant variability among individuals, the typical sleep cycle duration is about 90 minutes. The percentage of the cycle spent in REM increases as the night progresses while the percentage of cycle time spent in SWS decreases.

There are numerous physiological differences between REM sleep and NREM sleep. REM sleep is characterized by rapid eye movement, muscular atonia, dream content, fluctuations in autonomic function (irregular respiration, pulse, temperature, and blood pressure), a brain metabolic rate similar to waking, and desynchronized neuronal activity. There is neither noradrenergic activity nor serotonergic activity during REM. By comparison, NREM sleep is characterized by relatively little eye movement, muscle tone, little dream content, regular pulse, temperature, and blood pressure, relatively low brain metabolic rate, and synchronized neuronal activity. Further, in NREM increased tissue synthesis, cell division, and growth hormone release is observed relative to waking or REM stages. Many of these physiological differences can be monitored non-invasively so as to distinguish between REM and NREM sleep.

While there is still much to be learned about sleep, there are a few theories (not necessarily mutually exclusive) that have gained merit regarding the question "why do we sleep." The "adaptive theory" argues that sleep functions to increases the probability of an animal's survival (feeding, other predatory behavior, and avoiding danger). Support for this theory stems from the observation that sleep-wake patterns differ within species and are well suited for the species particular biological niche. The "Energy Conservation Theory" instead focuses on the idea that the reduced metabolic rate during sleep helps retain energy. Generally animals with high metabolic rates sleep longer than animals with slower metabolic rates. For the purposes of this discussion, however, we are most concerned with the widely accepted "Restorative Theory of Sleep," in which the general implication is that sleep plays an important role in revitalization.

Mechanisms underlying the restoration process include neutralization of neurotoxins that accumulate during waking hours, responses to increased sleep-inducing substances that are produced during waking processes, neurochemical synthesis, and brain chemical redistribution. During SWS, increased tissue synthesis, cell division, and growth hormone release is observed. Athletes have higher proportions of SWS than others. Oxygen consumption declines during SWS suggesting reduced catabolism. SWS increases after starvation in an apparent compensatory effect. Hyperthyroidism increases SWS whereas hypothyroidism reduces SWS, and SWS is high during peak physical developmental years in children and declines during advancing age. Last, research indicates that SWS has an intensity component. This intensity dimension of SWS apparently allows mammals to compensate for lost sleep without having to significantly increase sleep time. It is important to note, however, that is unclear if such an intensity dimension exists for REM sleep and thus it may be more difficult to compensate for lost REM sleep.

While NREM sleep, and in particular SWS appear to play a central role in physical restoration the purpose of REM sleep seems to be different. Although the current state of research does not support definitive answers, there are numerous compelling hypotheses regarding the purpose of REM sleep. Understanding the differences between REM and NREM sleep is key to the ensuing discussion and conclusions.

The lower metabolic rates and lower body temperatures of NREM apparently provide an environment conducive to neuronal repair. REM sleep does not serve the same purpose (neuronal activity is similar to that of waking activity), but it may serve yet another role: the restoring full sensitivity of monoamine receptors (especially those for norepinephrine, serotonin and histamine). This is accomplished by the cessation of monoamine neurotransmitter release during REM sleep (causing sleep paralysis and reducing environmental awareness).

Furthermore, the "Programming-reprogramming Hypothesis" claims that sleep (specifically REM sleep) serves to remove unimportant information and consolidates and strengths more important experiences. Evidence includes the fact that infants, whose brains are presumably experiencing significant change during development, sleep twice as much as adults, and much of this time is spent in REM. Other theories related to this hypothesis argue that REM sleep is important in memory (especially memory consolidation) and intellectual function. Studies show that REM sleep increases during intense learning experiences and that REM sleep deprivation leads to reduced creative problem solving ability.

Experiments have shown that perceptual skills, such as those that are learned through repeated practice, improve overnight and are disrupted if there is selective interruption of REM sleep. Other experimental data suggest that cerebral activation that occurs during REM sleep plays a key role in brain development.

REM sleep is additionally linked to proper functioning of active growth and development of the nervous system. The fact that REM sleep is resistant to age-related changes is believed to suggest a role in maintaining nervous system function. Moreover, while the purpose of dreaming (a key distinguishing feature of REM) is even less well understood than REM, many the theories about it reinforce the cognitive-health importance of REM sleep. These theories include proposing that dreaming (and thus REM) is intertwined with long-term memory consolidation of semantic memories, learning, and resolution of distressing experiences.

Of particular interest to those hoping to wake cognitively alert is yet another possible function of REM sleep. Mammals experience much more REM sleep than do reptiles. This may be related to the cold-blooded and slow-awaking nature of reptiles as opposed to the relative quick start of mammals. In this context, REM sleep is seen as a way for mammals to become alert quickly through REM-priming. That is to say that during REM sleep, relative to the other states of sleep, the brain is functioning most like its waking state, and thus the transition from sleeping to waking requires relatively little adjustment. By comparison, in Stage 2 the brain does not function like its waking state. In Stages 3 or 4 the brain functions even less like its waking state. The deeper the sleep (with Stage 1/REM being the lightest and Stage 4 being the deepest) the more dissimilar the brain's activity is relative to waking brain activity, with a pronounced difference between light NREM and SWS NREM (making the Stage 2/Stage 3 transition of particular importance in certain cases).

A phenomenon related to the transition from sleeping to waking that is key to our discussion is that of "sleep inertia" (also known as sleep drunkenness). It is a phenomenon that normally occurs in humans during the transition from sleep to wakefulness, and refers to a period of impaired performance (both cognitive and motor), reduced vigilance, general grogginess, disorientation, a propensity to want to return to sleep, etc. The impairment may be severe and may last anywhere from minutes to several hours. Studies have scientifically demonstrated the debilitating effects of sleep inertia, and have found the average duration to be between 1 and 3 hours depending on the time of waking (night wake ups lead to longer durations). The impaired performance attributable to sleep inertia has important implications for many activities, especially those that require rapid decision making following forced abrupt awakenings (for instance, an on-call doctor sleeping at a hospital) or for activities following naps.

While the cause of sleep inertia is still unknown (not to say that there are no theories), there are some key factors that seem to play a role in influencing the potency of the effect. One of the main factors is thought to be the depth of the sleep at the time of waking; the deeper the sleep the worse the sleep inertia. While the reason for this correlation is unknown, there is reason to believe that it is related to the difference in brain function during stages 1 through 4 relative to waking, and the related REM-priming discussed earlier. The difference between light NREM and deep (SWS) NREM is then of particular importance to determining the effect of sleep inertia because SWS NREM brain activity contrasts starkly with waking activity. This is not to say that Stage 1 and Stage 2 activity are similar to waking activity, rather it highlights the transition from light to deep sleep (and the resulting sleep inertia effects) as being more abrupt than one might expect; a few minutes difference in wake time relative to the sleep cycle can significantly affect the strength of the sleep inertia. It is from this understanding of sleep inertia that some suggest the best nap is a brief one (10 to 30 minutes). The idea is that the subject wakes before entering SWS, which generally occurs a little more than 30 minutes into the sleep cycle.

Another factor which influences sleep inertia is the timing of the sleep. Studies have shown that more sleep inertia results when waking near a trough in the body temperature (which cycles throughout the day). By contrast, subjects often experience less sleep inertia when waking near a body temperature high.

The body's temperature cycle is directly related to the phase of the circadian rhythm (the body's natural daily rhythm). Under proper conditions, the body temperature cycle, the circadian rhythm, and the sleep-wake cycle stay relatively consistent (generally the body temperature nadir occurs between the third sleep cycle and approximately two hours before the subjective wake time). The phase of the sleep-wake cycle is able to shift more rapidly than the circadian rhythm phase (and its underlying body temperature cycle), which can result in the minimum body temperature occurring at different times relative to the subjective wake time. Jet lag is the result of a significant shift between the sleep-wake cycle and the circadian rhythm. Shift work can also lead to the two cycles falling out of synchronization. The changing environment can also play a role, especially in cases such as Seasonal Affective Disorder (SAD). Disruption of the thermoregulation and sleep-wake cycles may lead to problems both initiating and maintaining sleep, abnormal sleep architecture, and resulting daytime sleepiness.

The human circadian rhythm, when allowed to cycle without outside stimulus, varies from just under 24 hours to more than 27 hours in length with the average falling at about 24.5 hours. Under the influence of outside stimulus, the circadian rhythm can be "entrained" (influenced) in such a way that its duration can be extended or shortened, and its phase shifted relative to other cycles. Of the possible environmental stimuli that can work to "entrain" the circadian rhythm, light is far and away the dominant synchronizer for the circadian pacemaker, including phase shifts. The suprachiasmatic nucleus (SCN) in the anterior hypothalamus, dorsal to the optic chiasm serves as mammals' master pacemaker for circadian rhythms. Photic information is relayed to the SCN via the retinohypothalamic tract. Further, studies have shown that a specific subset of light is particularly effective at resetting the circadian rhythm, specifically blue/green light in the range of 420-500 nm.

Greater light intensity has been shown to produce greater circadian shift. However, equally important in obtaining a desired circadian shift is the timing of the exposure. As noted earlier, when the circadian rhythm is properly synchronized with the sleep-wake cycle the body temperature minimum occurs about five to six hours after usual bedtime (about two hours before usual wake time). The body temperature minimum will stray farther from this synchronized point as disruption of the circadian and sleep-wake cycles becomes greater. Of particular importance to our discussion is that the body temperature minimum is theorized to provide an inflection point which determines the circadian-phase-shift direction caused by light exposure. That is, studies show that light exposure before the temperature nadir delays the circadian phase, extending the day, causing a later wake-up time and later sleep onset. By contrast, light exposure on the dawn side of the temperature nadir (after it occurs) has been show to phase advance the circadian rhythm, causing earlier wake-up and sleep onset.

The so-called "Phase Response Curve" (PRC) illustrates the relationship between the timing of light exposure and the effect on the circadian rhythm. The studies that have led to the PRC indicate that for much of the day, light has little effect on the circadian rhythm. Light begins to have a phase delaying effect about seven hours before the body temperature minimum (about two hours before the usual bedtime). The effect strengthens from a phase-shift of a few minutes to phase-shifts as great as two to three hours as the exposure time gets closer and closer to the body temperature minimum. The PRC peaks just before the temperature minimum at which time the inflection point shows the abrupt change from phase delay to phase advance. Exposure a few minutes before the temperature minimum is theorized to produce the most pronounced phase delay (up to two to three hours) while light exposure a few minutes after the temperature minimum is theorized to produce the most pronounced phased advance (also up to two to three hours). After this abrupt inflection point, light exposure for approximately the four hours following the temperature minimum affect circadian phase advance with the most effective times being closet to the temperature minimum. After these approximately four hours (about two hours after usual wake up time) the phase shift effectiveness again falls to near zero. There is still much to be learned about circadian phase entrainment, but the inflection point created by the body temperature minimum seems to be key.

Given the limited and simplistic nature of existing alarm clocks, for most individuals it is to a large extent chance as to which stage he or she will be in when the alarm clock goes off. It is an all too common occurrence to be awakened while in a deeper sleep stage. When this occurs, it is common for the awakened individual to subsequently suffer the mal effects of sleep inertia, which drastically decrease a person's awareness, effectiveness, and efficiency. There is a clear need for an intelligent system which is capable of monitoring the sleep cycles of its user such that the user can be awakened at the time that best maximizes his or her alertness and energy in a efficient and productive manner.

The manner in which a person is awakened is also important in seeking to optimize alertness and energy. Not only does some research show that gradual awakenings are preferable to abrupt awakenings, but as noted earlier, it is well known that exposure to light when waking, especially light directed at the eyes and other particular parts of the body, are important in resetting the body's circadian rhythm, or "natural clock", to maximize the alertness and "awake" feeling of the subject. A system that can additionally appropriately entrain the circadian rhythm (whether it be the daily struggle to phase-advance the circadian rhythm from its natural 24-plus hour duration to the earth day's 24 hour cycle or the even more greatly desynchronized jet-lag-suffering or shift-work subject) will prove all the more beneficial to this end. Thus, there is an advantage to waking the user through the use of a simulated sunrise achieved via the ramping up to full brightness a source of illumination.

PRIOR ART AND OBJECTIVES

U.S. Pat. No. 4,858,609 to Cole is a bright light mask for shining a high intensity light into a subject's eyes at preselected time period to modify circadian rhythms. This reference is an early example of the understanding that light directed as an individual via a mask worn by the individual may be used to modify the individual's circadian rhythm.

U.S. Pat. No. 6,928,031 to Kanevsky et al. discloses a programmable alarm clock to identify and wake a person during non-REM sleep patterns. Using brain activity sensors attachable to a head of a sleeper, a signal is sent to a local computer, which identifies REM sleep periods and non-REM sleep periods. Then, the local computer adjusts the wake-up time to coincide with a non-REM sleep period, if necessary and if possible.

Although Kanevsky states a goal of awakening sleepers during NREM sleep, it does not detail the differences of awakening the sleeper in light NREM sleep (i.e. stages 1-2) or deep SWS NREM sleep (i.e. stages 3-4). As noted above, an individual generally experiences increased debilitating effects when awakened during the deeper NREM sleep stages. Thus, Kanevsky fails to consider the importance of waking an individual directly after REM sleep so that the individual is already in the lightest stage of non-REM sleep. Kanevsky discusses that an individual will experience more subsequent drowsiness and debilitating effects when woken during REM sleep rather than if woken during NREM sleep. Kane sky's assertion that sleep inertia results from REM sleep awakenings teaches away from the present invention which is based upon the idea that sleep inertia is worst during deep sleep awakenings. Kanevksy's assertion implies that in order to minimize sleep inertia it is better to wake the individual during slow wave sleep rather than during REM sleep; this is counter to the present invention.

U.S. Pat. No. 5,507,716 to LaBerge et al., discloses a means to assist an individual to achieve lucid dreams by detecting and monitoring eye and head movements for the presence of REM sleep in the individual, and then applying sensory stimuli to a sleeper in REM sleep. IR emitter-detector pairs are used, one for sensing eye movements and one for sensing body movements and components that produce a low intensity sensory stimuli. A microprocessor in LaBerge monitors the fluctuating voltage from the infrared signal for the occurrence of a predetermined sequence of voltages to trigger the stimulus producing components. LaBerge et al. is not intended to be used as an alarm system, and does not take into account factors such as the phase response curve or even whether it is the subject's first REM cycle or the subject's last. Furthermore, LaBerge et al. discloses providing a stimulus during REM with no intent to provide stimulus thereafter. That LaBerge et al. provides stimulus at conceivably any or all of the REM cycles throughout the night might either prematurely wake the subject and/or lead to sleep fragmentation. Studies have shown that brief arousals during the night, which LaBerge et al. could create, cause performance decrements similar to sleep inertia and increased sleepiness. Moreover LaBerge et al. uses a predefined method of detecting REM sleep rather than the relative method employed in the present invention. Last, LaBerge et al. uses a mask connected to a base station that prohibits easy portability and free range of movement during the night.

U.S. Pat. No. 7,248,915 to Rönnholm, discloses a means for determining a time when an individual should be awakened. A receiver disclosed in this reference receives a sleep descriptor, one such sleep descriptor being REM sleep. The reference also discloses detecting the end of REM and providing a stimulation signal to the individual at or after the end of REM but does not specifically ensure that the last possible REM cycle will be chosen. Furthermore the Rönnholm claim by which light stage sleep is maintained for extended durations of time might lead to sleep fragmentation and resulting debilitating effects previously discussed. Last there is no discussion of circadian phase, its relation to the phase response curve and the related effect on entrainment, sleep, and the resulting alertness and performance capability upon waking.

U.S. Pat. No. 4,863,259, to Schneider, discusses a means for detecting REM sleep, and further awakening a sleeper within a predetermined interval of time after the end of detection of said REM sleep. Schneider fails to distinguish between light NREM sleep and deep NREM sleep, and therefore could easily awaken a subject in the midst of the subject's deepest sleep. Although Schneider does briefly discuss waking a subject during REM or shortly thereafter, he does not distinguish between waking the subject during the first REM cycle, the last REM cycle, or any between. Moreover, much like LaBerge et al. the indicators claimed could lead to premature awakenings and/or lead to sleep fragmentation. Like LaBerge et al. Schneider uses a fixed threshold method of detecting REM sleep rather than a relative one. Further, Schneider makes no mention of circadian phase or entrainment with regard to appropriately waking the subject. Last Schneider also employs a device that might shift during nighttime movement or might prevent free range of movement during the night. In that way, Schneider has taught away from the present invention, which takes into account the circadian phase implications of the phase response curve and awakening a subject at a time more specific than would be understood from a reading of Schneider.

Thus, none of the prior art provides a means of providing an alarm system for waking an individual at the optimum time in an individual's sleep cycle. A typical sleep cycle goes in and out of light stages of sleep repeatedly, and none of the prior art, either alone or in combination, provides a means for determining that an individual is in a light sleep stage and that the individual is in a cycle wherein if awakened the individual's circadian rhythm would be optimally entrained. Further, the prior art fails to consider the manner in which the individual is awakened and how this might affect the individual's circadian rhythm.

It is thereby an objective of the present invention to provide a method of monitoring the sleep cycle of an individual and awaking the individual at the optimal time and in the best manner.

It is a further objective of the present invention to provide a device for awakening an individual within approximately one complete sleep cycle of a preset time selected by the individual.

It is a further objective of the present invention to monitor an individual's REM sleep along with the individual's body temperature so as to awaken the individual at an optimal time considering both factors.

It is a further objective of the present invention to provide a device for awakening an individual with appropriate stimuli as related to the present phase of the individual's circadian rhythm.

It is a further objective of the present invention to provide a device for monitoring REM movement that is comfortable for the wearer to use while the wearer sleeps, thereby permitting the wearer to sleep naturally.

SUMMARY OF THE INVENTION

The present invention provides a system for optimizing an individual's time spent sleeping and for providing a timed wake up alert to minimize the pitfalls of sleep inertia and to leave the individual feeling energized, thusly maximizing the productivity of the human sleep cycle. In detail, a user's sleep cycles, including the Rapid Eye Movement ("REM") are monitored such that the user may be awakened at the best time and in the best manner in order for the user to feel well rested.

In its simplest form, the present invention provides for an infrared (IR) emitter, a photodiode, and a computer that monitors the signal from the photodiode to detect eye movement through a closed eyelid. In the preferred embodiment of the invention the eye movement is detected using novel eyewear that is comfortable for the individual to wear while sleeping.

The computer analyzes many of the signal's parameters, including the variations in signal amplitude. An increase in signal variation indicates eye movement and thus REM sleep.

In order to not awaken the individual prematurely, the system will in a preferred embodiment not interrupt sleep until the last expected sleep cycle before a predetermined wake time. As individual cycles vary from person to person, the system over the course of the subject's use determines that user's average sleep cycle length, and calculates backwards from a preset wake time. For instance, if the system calculates that for a given user the average sleep cycle lasts 90 minutes, it will not awaken that user any more than 90 minutes from the user's preset wake time entered into the system. In other embodiments, a set time for monitoring may be employed, wherein regardless of user, the system will not begin monitoring outside of a predetermined time window. The analysis window can be adjusted for individual subjects. When the invention detects a REM stage, it subsequently wakes the subject upon the end of the detected REM stage.

Finally, the method, instead of waking the user utilizing the standard startling effects of the modern alarm clock buzzer, employs a more gradual, natural awakening. In a preferred embodiment the system includes an LED display, directed at a subject's eyes that slowly increases in brightness over an extended period of time so as to gradually wake the individual in a manner similar to a morning sunrise. As noted in depth previously, a gradual light stimulus has many benefits including resetting the body's "natural clock," (the circadian rhythm) and to maximizing alertness. The system could include a back-up audio alarm to wake the sleeper at a specified must-wake time if the lights fail to wake the subject.

BRIEF DESCRIPTION OF THE DRAWINGS

The foregoing aspects and many of the attendant advantages of the invention will become more readily appreciated as the same becomes better understood by reference to the following detailed description, when taken in conjunction with the accompanying drawings, wherein.

DETAILED DESCRIPTION OF THE INVENTION

Figure 1:
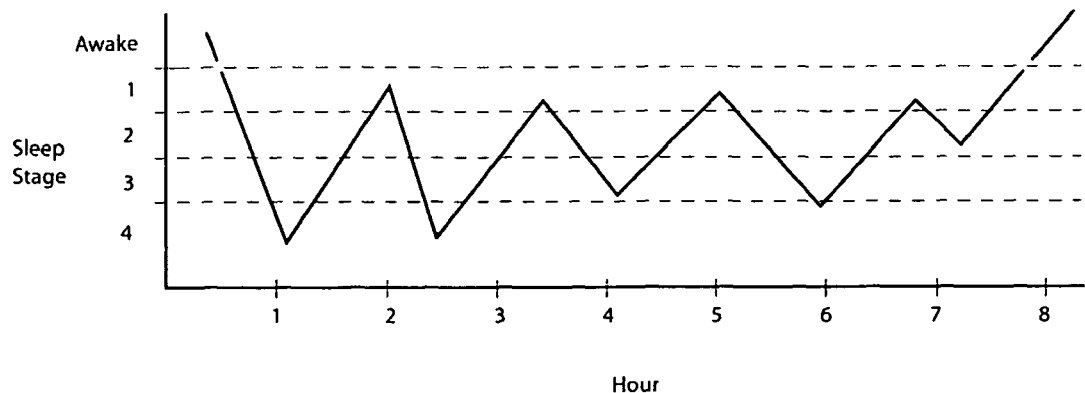
FIG. 1 represents the progression of the sleep cycle through a normal night of sleep.

Objects and advantages of the present invention will become apparent from the following detailed description taken in connection with the aforementioned accompanying drawings. It is to be understood that the invention is not limited to the details disclosed but includes all such variations and modifications as fall within the scope of the appended claims.

In its basic form the applicant's claimed apparatus and method for using the same employs a simple means for detecting REM. An IR emitter and photodiode are mounted on the inside of a pair of glasses, positioned apart from one another but both generally facing toward the eye. This method of detecting REM is not novel and is discussed extensively in the cited prior art. In a preferred embodiment of the invention the device is of the form of a structured sleep mask. This allows a mammal (preferably a human) that is wearing the device to still feel free to sleep naturally (i.e. on one's back, side etc.). The prior art has revealed masks/glasses that have attempted to allow the wearer increased comfort without detracting from the ability of the device to capture data, but the prior art requires a physical tethering to a base station of some sort that serves to collect the data. The present invention moves the computing power and data collection to the device itself, so that no tethering is necessary. Wireless transmission allows data to be transferred out of the device without requiring a physical tethering of the device that would likely disturb the user as he or she slept.

As discussed in the prior art, as the IR emitter bounces IR light off the wearer's closed eye, the photodiode picks up scattered reflection. When the eye is not moving, the eyelid reflects the IR beam back to the photodiode in a relatively constant manner. When the eye moves, however, the angles of reflection are constantly changing and thus the amount of IR light received by photodiode varies. In the preferred embodiment, all necessary input, power and computing capacity is onboard the equipment worn by the subject, but alternatively such components could communicate with an external computer via wire, Bluetooth, other wireless protocols, or some combination thereof.

By analyzing the maximum and minimum voltage (peak to peak) recorded in one hundred samples every second, and finding the difference in these values, the system creates a data point that represents the amount of variance, or signal variation every second. The variance is proportional to the amount of eye movement during a set time frame, the set time frame in a preferred embodiment being 1/100th of one second. The system averages this running data for variance over time and compares recent values with past values, looking for a jump or decrease in variance that signifies eye movement or cessation of eye movement. In short, the amount of variance at a second time interval is calculated relative to the amount of variance in a first time interval. Once a threshold change in signal variation is attained, the system determines that REM is occurring. Likewise, once the movement of the eye drops below the threshold change in signal variation, the system determines that REM has ended.

Figure 3A:
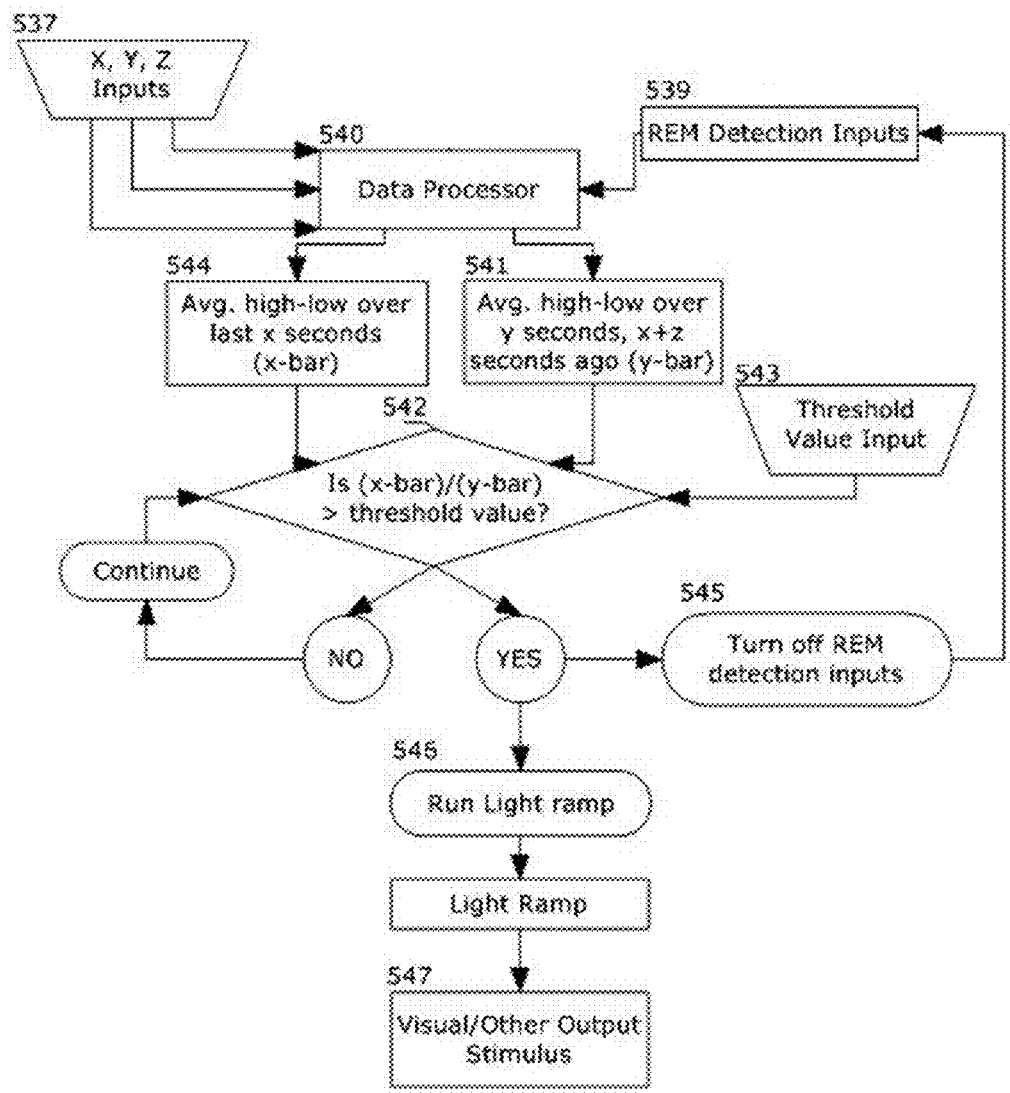
FIG. 3a is a block diagram illustrating the logic flow of the invention.

Turning to FIG. 3a, in practice the only steps required of a user are setting a wakeup time. Once this predetermined wake up time (predetermined time) is set, the user positions the device over his or her eyes and sleeps. The system then continuously compares the predetermined time with the current time. The system has a third time stored in its memory, that time being the maximum number of minutes before the predetermined time that the system will be monitoring the user's physiological data. At any time before the maximum number of minutes before the predetermined time, the system in a preferred embodiment is not monitoring the user's physiological data. Once inside the window of time between the predetermined time and the maximum number of minutes before it, the system begins monitoring for physiological data. The maximum number of minutes may range from between 60 and 120 minutes, but in a preferred embodiment is between 90 and 110 minutes.

While the beginning analysis window time (in a preferred embodiment somewhere between 90 and 110 minutes before the predetermined input time) is fully adjustable to allow for individual preference, it is generally best for the window to be approximately the same duration as the length of one sleep cycle of the user. The reasoning for this is that such a window will be long enough to capture the last REM cycle to occur before the predetermined wake up time but short enough (not more than one sleep cycle) to avoid detecting the penultimate, or perhaps even earlier, REM sleep period prior to the predetermined wake time.

Although detecting and acting upon earlier instances of REM sleep can be useful as described in the prior art (see LaBerge et al. for lucid dreaming and Schneider for identifying REM sleep throughout sleep), it poses numerous potentially detrimental outcomes for the alertness, performance, and cognitive function of the waking subject—the exact benefits for utilizing the present system. Thus, by using an analysis window of approximately one sleep cycle prior to the wake up time, the system avoids possible inducement of sleep fragmentation, loss of extra sleep, and helps to ensure all possible REM cycles are fully obtained and completed by the user. As discussed previously, REM sleep is particularly important for numerous cognitive and other functions and also for maximizing alertness and performance capability. Thus monitoring and waking the individual during the period of time between the predetermined wake time and a maximum time before it is crucial in ensuring the best wake up possible.

Figure 2A:
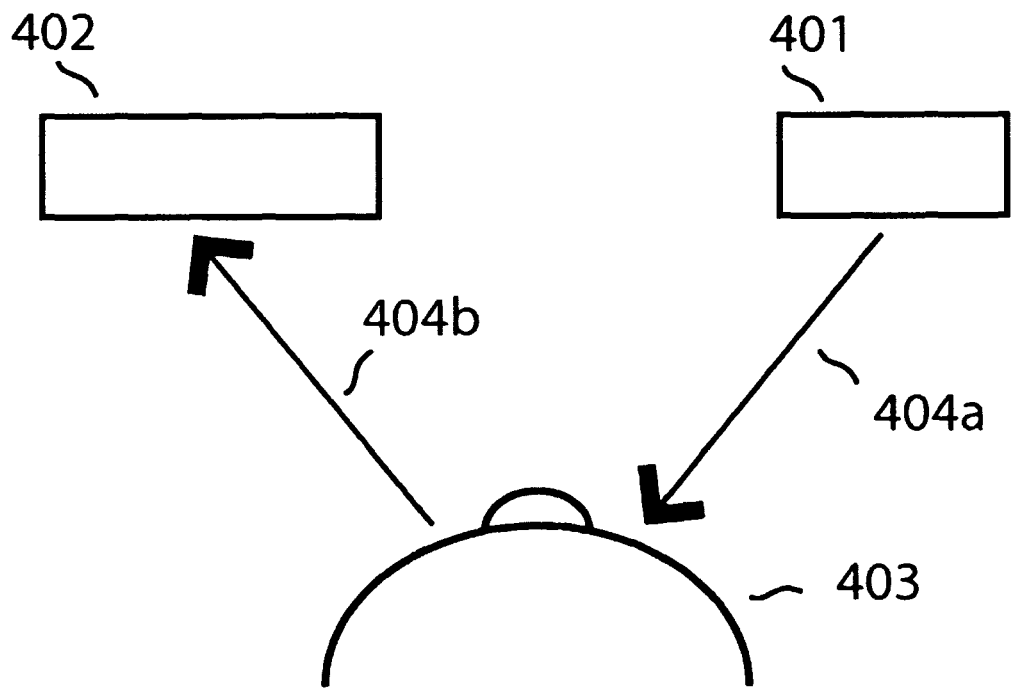
FIG. 2a is an illustration of the relatively constant beam reflection when the eye is not moving.
Figure 2B:
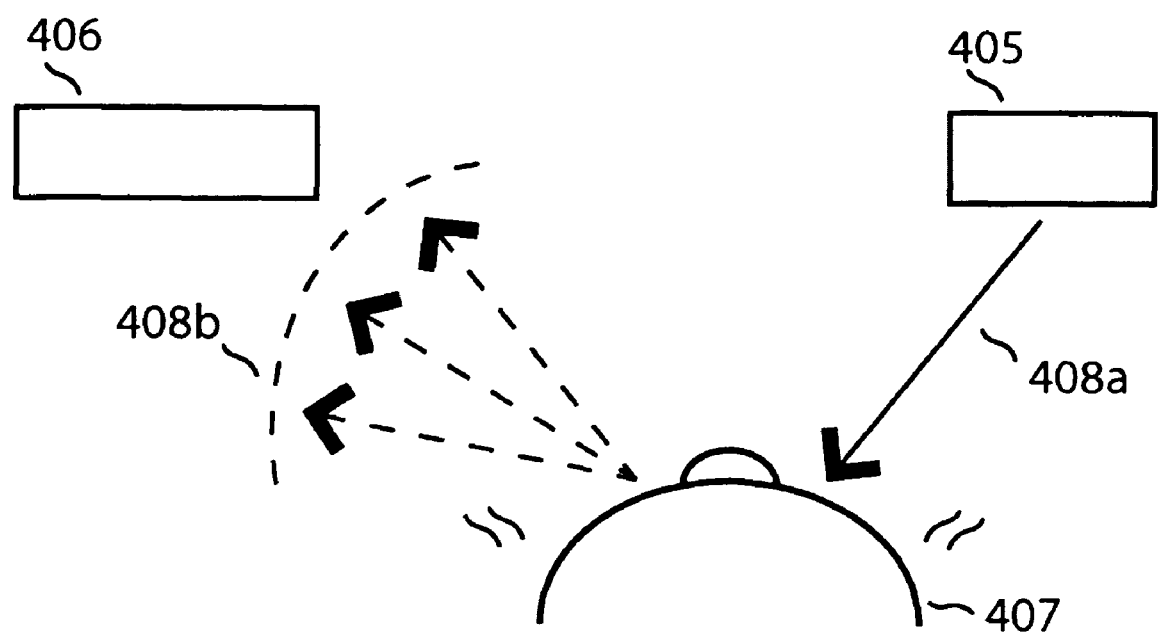
FIG. 2b is an illustration of the variable beam reflection when the eye is moving.

During the window of time described above, the system activates the IR emitter 401 by supplying a constant voltage of 2V to the IR emitter through a digital to analog converter (DAC). IR emitter 401 which is attached to the inside of the input goggles, shines light 404a towards the user's closed eye which reflects a portion 404b of said light towards the photodiode 402 with various intensities depending upon the movement of the eye (FIG. 2a and FIG. 2b). The invention reads the voltage across the photodiode through an analog to digital converter (ADC) one hundred times per second. The system then calculates the maximum variation in voltage across the photodiode in each second by calculating the difference between the highest and lowest voltage recorded in each second. For purposes of this patent application, this difference between the highest and lowest voltage shall be termed "variance", and is representative of the amount of eye movement during a time interval, and thus the amount of REM, which in turn correlates to the user being in the REM sleep stage.

Figure 3B:
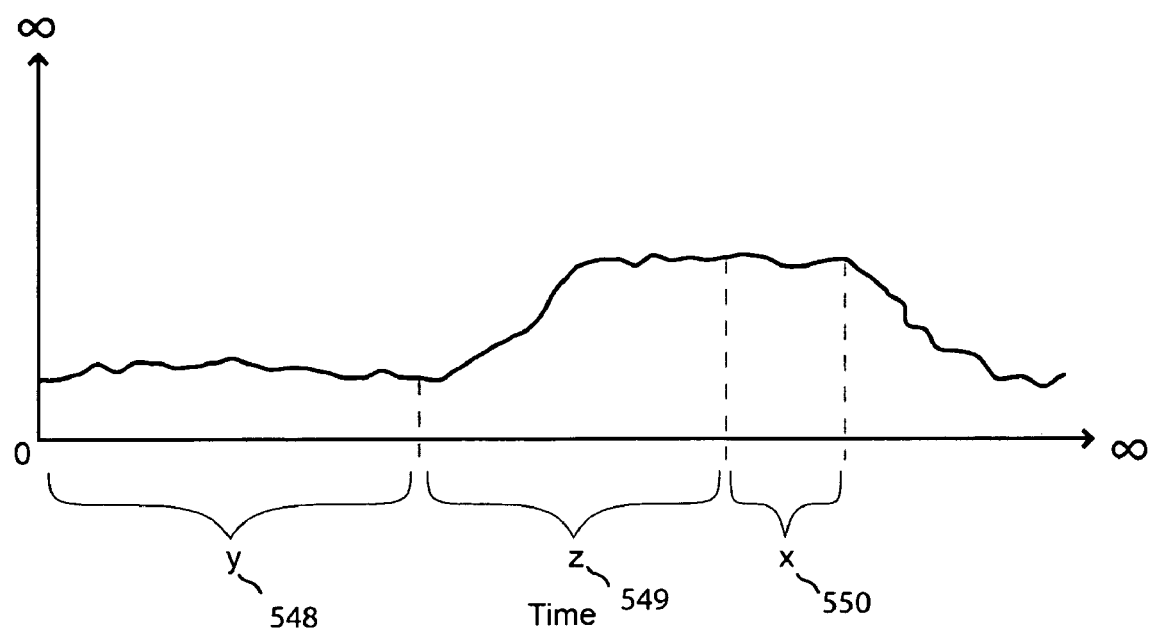
FIG. 3b depicts the three time intervals that the system uses in determining the occurrence of REM.
Figure 3C:
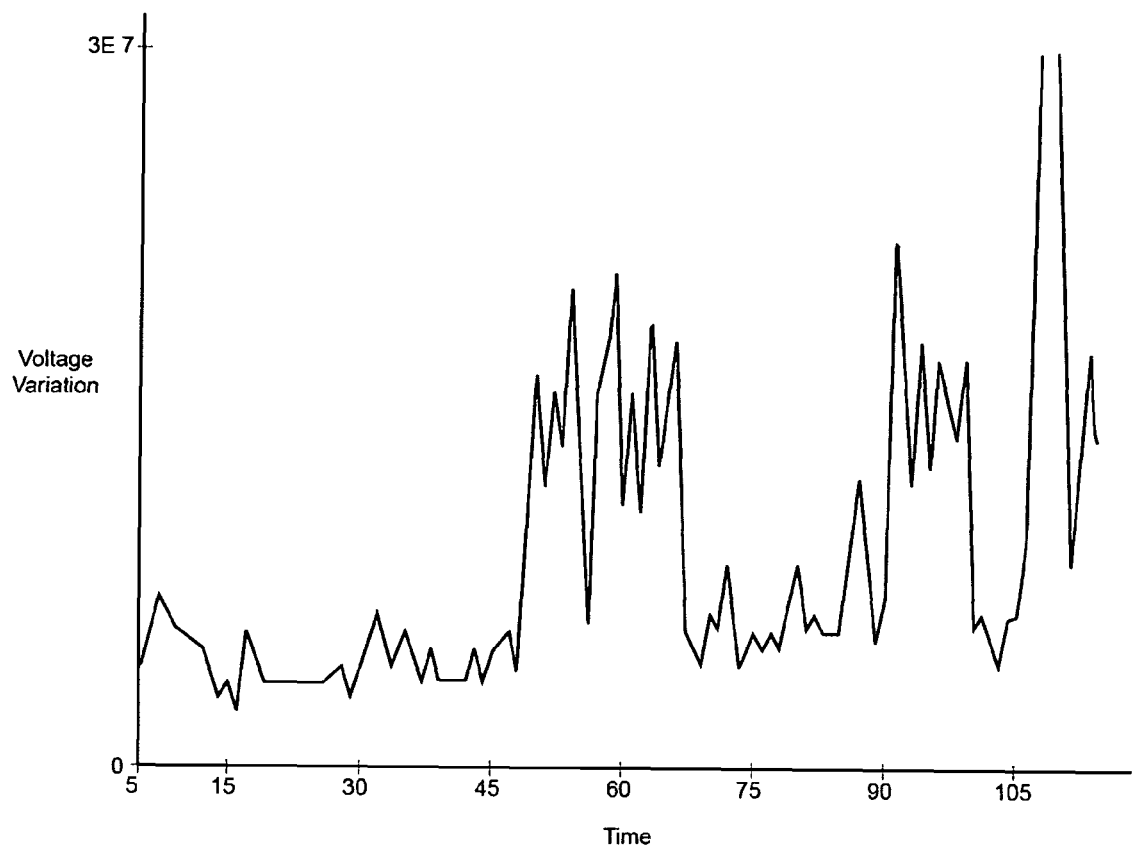
FIG. 3c is experimental data showing signal variation during periods of eye movement and periods of no eye movement.

A new maximum variation data point is generated every second, and these data are sorted into various arrays. The overall maximum variation history or other such data may optionally be displayed via a display means in wireless communication. FIG. 3c is an exemplary figure showing voltage variation on the y-axis and time in minutes on the x-axis. Period of REM sleep are easily discerned in this drawing as tall spikes.

Once the system begins monitoring for REM sleep, a data processor 540 constantly calculates two additional values each second. The first is the average voltage variation over the last X seconds, 544 [550]. This value is indicative of the most recent signal variance. The second value is the average voltage variation over Y seconds, X+Z seconds earlier, 541 [548]. While values, X, Y, and Z are fully adjustable 539, generally Y will be large relative to X. This leads to a longer averaging period than the X average 544 (which is intended to give a picture of current variance). The reason for the Y average 541 to be longer is because it is used as a baseline variance; that is it is usually indicative of the average signal variance during NREM sleep. The analysis window of the Y average 541 is shifted earlier by the addition of a buffer time, Z seconds 549, between the most recent edge of the Y average 541 window and the oldest edge of the X average 544. The intent here is to ensure that when possible the two values contain data distinguished by its difference, not its similarity. Looking at FIG. 3b, one can see that if not for the butter time, Z seconds 549, the Y average 541 would include a significant amount of higher signal variance. Such a result would make it more difficult to discern when current activity is different from past. By comparing these two values 542, the invention can detect jumps in variation. A key innovation to note is the relative manner of detection rather than using hard threshold values. There is no set variance that is indicative of REM sleep or NREM sleep; rather the system calculates the percent increase/decrease of the first value 544 relative to the second value 541 and compares this with a customizable input value 543 that signifies the minimum percentage change associated with the beginning or end of rapid eye movement 543. This relativistic method provides for automatic calibration to determine the cessation of REM in different individuals and even different placements of the system on the same individual (thus it is not critical to wear the system in the exact same location very night) because it is not the variance that is critical, rather the change in variance of the X average 544 relative to the baseline Y average 541.

It is important to note that the above percentage analysis 542, does not begin to occur until X+Y+Z seconds have passed since the system started to monitor for REM sleep. This is because it takes this long for the two calculated values 544 541 to reach reasonable and non-zero values. This lag time is included when setting the appropriate beginning of the analysis window to the duration of approximately one sleep cycle before the wake up time.

The detection of REM sleep triggers the final stage of the program 546. The LED ramp increases the DC output of the DAC from the "Starting LED Voltage" value (LEDs off) to the "Necessary Max LED Voltage" value (max brightness) over the user-defined number of minutes, "Simulated Sunrise Time (minutes)" . The program adds 500 μVs per iteration and automatically sets the time delay of the iterations in order to reach the maximum brightness in the desired amount of time. The program also displays a countdown of the "Seconds Till Max LED Brightness" for atheistic reasons. The ever-increasing DAC output is connected to an array of LEDs 547 wired in parallel and directed at a subject's eyes in order to wake the individual. Although in this preferred embodiment the LEDs direct light at the user's eyes, in an alternative embodiment a dimmer control interacts with one or more lights in the user's room. For instance, the device could dim the one or more lights as the user progresses toward sleep and could increase the light level to wake the user. Furthermore, in addition to the aforementioned benefits to a gradual awakening provided by a slowly brightening visual stimulus, it also provides a built-in safe guard against waking the subject during REM (in addition to the inventions described method of detecting the conclusion of REM) and automatically interacts with the body's natural tendencies to wake the subject as the most natural time, after transitioning out of REM. The reason for this is that the arousal threshold during REM sleep is relatively high whereas during Stage 1 and Stage 2 sleep it is relatively low. Thus even if the LED ramp begins during REM sleep, the fact that it begins with an extremely small stimulus means that in all likelihood it will be unable to wake the individual during REM sleep. While the lights are still relatively low there is very little chance of a REM awakening, however, after the transition to light NREM and with it the subject's significantly reduced arousal threshold, the stimulus' likelihood of waking the subject will increase dramatically, especially as the stimulus continues to increase.

Additional means for waking the user are also contemplated, such as a vibration stimulus alarm or an auditory stimulus alarm, wherein for each of these the user can select the stimulus as either the primary means of alarm, a backup in the event the primary means fails to wake the user. Finally, any combination of disclosed sensory inputs to the user may be used either as a primary means for waking the user or as a backup.

Although in the preferred embodiment of the invention, the sleep mask is disclosed and all components are mounted thereon, in a first alternative means of detecting eye movement the system is based on a headband input device that suspends the necessary LEDs and photodiodes over the wearer's eyes. In another alternative means of detecting eye movement, the system uses a similarly sleep mask but one that allows the subject to see out whether by a set of clear lenses above the eye or simply an opening above the eye or other means. In another form, the necessary components are attached to only the top rim of the mask/goggles with suspended LEDs and photodiodes above the eyes; basically it is a paired down, less bulky take on the full version that provides similar monitoring and stimulus capabilities without obstructing the subject's view. In another form, the necessary components clip onto a subject's preexisting glasses. Additionally, it would also be possible for one or more detectors mounted near the user's bed to detect eye movement through the eyelid without any device mounted to the user. There are numerous alternative means of detection along these lines including optical recognition, thermal imaging, and optical recognition therein. The use of IR illumination, a thermal video camera, and/or low-level light video camera in combination with said optical recognition software embody detection methods that do not necessarily need to be attached to the subject.

As described in the preferred embodiment of the invention, no initial setup or calibration is necessary because the values used are relative to other values detected. However, in an alternative embodiment of the invention hard threshold values may be used in place of relative ones, as has been described in the prior art. For instance, preliminary testing of a subject could determine a definite value for the subject's signal variance during NREM sleep and another definite variance value for the subject that indicates REM sleep. These hard values would be used instead of the relativistic percentage comparison to determine if the subject is in NREM or REM sleep.

Although in the preferred embodiment of the invention, only eye movement is detected, in alternative embodiments of the invention other physiological markers could be detected as well. For instance, an additional IR LED/photodiode pair may detect overall body movement. During REM sleep the body is paralyzed, and the detection of lack of movement of the user would suggest the user is in the stage. Using this sensor in combination with the IR LED/photodiode pair directed at the eye, improves the accuracy of REM detection. The detection of body movement would prevent false detections of REM sleep because a REM stage in all likelihood is not occurring if body movement is simultaneously detected. Similar to this, Non-IR based vibration and movement sensors may be used for the same purpose. Such sensors may be attached either to the bed or sleeping area of the user, or to the user's clothing directly.

Finally, during REM sleep the body's ability to thermoregulate lessens, and thus body temperature variations are an indicator of REM sleep. Accordingly, a temperature sensor may be employed in another alternative embodiment of the invention. As above, the temperature may be external or monitored through a wireless temperature monitor system, or to temperature recorders directly attached to the user. Myriad devices for recording the body temperature of a mammal are well known, and any will work with the described system. Much like thermoregulation, as discussed above, there are numerous measurable physiological data which exhibit distinctive characteristics while the subject is in REM as opposed to NREM sleep. These physiological differences between REM sleep and NREM sleep (including muscular atonia and irregular respiration, pulse, and blood pressure) present similarly to eye movement in REM relative to NREM, that is they are characterized by an increase in variation. Thus the invention and method already described lends itself to adopting the same detection approach for these various physiological factors.

Although the above physiological changes distinguish REM sleep from NREM sleep, the preferred alternative embodiment of the invention utilizes temperature in the analysis. This is because the preferred embodiment of the invention described above, when modified to take into account the body temperature of the sleeper, can provide additional benefits, albeit at the expense of simplicity. "Sleep inertia" is additionally affected by the wake-up time relative to the circadian rhythm as expressed in core body temperature. In short, one feels more rested when waking during a circadian temperature high and suffers the most from grogginess, etc. when waking during a temperature low. More important to the stimulus side of the invention is the fact that, as discussed in depth previously, the body temperature nadir produces an inflection point in the phase response curve of the circadian rhythm when entrained by photic stimulus.

Thus monitoring for the temperature minimum allows the system to determine whether it is best to apply photic stimulation as the means of waking, or some other stimulation so as not to disturb the user's circadian rhythm. In the everyday case of simply entraining the circadian rhythm to the earth day, this means using the photic stimulus to wake the subject if the detection of the last REM cycle before the desired wake time occurs after the body temperature minimum. Such timing leads to photic stimulus not only gently waking the subject but also providing circadian entrainment that makes the body better able to function at the desired wake time. If said REM cycle were to occur before the temperature minimum, the application of photic stimulus would have the exact opposite effect desire, instead of making it easier to wake and adjust to the day, the light would work to delay the circadian rhythm and delay the natural wake time even later. In such cases that the last REM cycle before the desired wake time occurs before the body temperature minimum the system functions more beneficially to the subject to use a non-photic stimulus to wake the subject. It thus avoids the reverse circadian-entraining effects desired because non-photic stimuli are far less effective at entrainment than photic stimulus. In the case of subjects suffering from the resynchronization of circadian and sleep-wake cycles, such as in jet lag and shift work, it may prove beneficial to promote circadian phase delay rather than the more standard circadian phase advance discussed above. Such instances would dictate that the invention provide photic stimulation if the last REM cycle before the desired wake time occurs before the body temperature minimum and non-photic stimulation if said REM cycle occurs after the body temperature minimum. Due to this additional need, the invention's decision processing can be adjusted (as simple as reversing the desired stimulus used) to individual subject circumstance. Additionally mentioned stimuli (such as controlling the brightness of the room lighting, etc) can be adjusted accordingly as well. In yet another embodiment, the photic stimulus (either within the device attached to the subject or any outside stimulus controlled-room lights, etc) would still function, but on a delay so as to occur after the body temperature minimum. In practice, the subject would awake to a non-photic stimulus and a relatively dark environment, some time after waking when the body temperature minimum has passed, photic stimulus is then applied to achieve the desire circadian entraining effects.

To optimally affect the user's circadian rhythm, an LED or other light-producing display is directed at the subject's eyes with the specific wavelengths and brightening pattern best suited to entrain the circadian rhythm (theoretically this is very similar to mimicking a sunrise with blue/green light in the 420-500 nm range). This both resets the user's circadian rhythm and maximizes the stimulus to wake the user. The light source(s) will either shine directly on the subject's eyes, reach the subject's eyes through reflection off another surface (for instance: the inside of the sleep mask being colored light-blue or another stimulating color and illuminated), or a combination of both. The benefit of this localized visual stimulus alarm, in addition to the non-startling and circadian rhythm resetting benefits already mentioned, is that it does not affect others in the room and provides the necessary light levels to affect the subject's circadian rhythm.

LEDs designed to appropriately stimulate the circadian rhythm and improve REM sleep duration and quality throughout the sleep cycle(s). Research has shown that light stimulus applied to various portions of the body can beneficially affect sleep quality, and aid in resetting the circadian rhythm (this is very important for individuals suffering from jet-lag, SAD, night-shifts, etc.). Such stimulus outputs may be located near the input system, or may be separate entities placed elsewhere on the subject and controlled either remotely via wire, Bluetooth, or other means, controlled locally, or a combination of both.

Although the primary use of the applicant's system and method will likely be with regard to nighttime sleep, it can also be used for nap analysis and as an alarm for a short nap of a subject. It is well known that naps can be very beneficial when timed correctly (both in the time of day relative to the circadian rhythm, and the duration of the nap). Because of the nature of the sleep cycle, the optimum length for a nap is either for less than 25 minutes or between 80 and 100 minutes, so as to ensure the nipper awakens during light sleep. During napping, at the user's preference, the system may actively monitors the user's sleep cycle and awaken the user either before they enter deep sleep, after the first REM cycle, or on a relative body temperature high, or a combination between these three as preferred by the subject.

In an additional alternative embodiment, the device comprises a smart snooze feature. Using this optional component, the device recognizes if the last REM cycle occurs at the beginning of the wakeup window (that is, close proximity in time to the maximum number of minutes before the predetermined wakeup time.) If the REM cycle occurs during that time (preferably within 15 minutes), the device still fully awakens the user, but then allows the user to fall asleep for approximately 25 minute "snooze" periods, briefly fully waking the individual up to three times before the final desired wake-up time. Each wake-up forces the user to restart the sleep cycle (thus restarting in the lightest stages of sleep), allowing the user to gain additional sleep without waking during slow wave sleep or deeper stages of light NREM. This allows the users to avoid suffering the debilitating effects associated with sleep inertia while still obtaining more sleep than an a wake-up during the early portion of the analysis window would otherwise allow.

Finally, in a final alternative embodiment of the invention, the system tracks nightly sleep cycles. By running constantly throughout the night and only recorded REM movement and/or body temperature, but not waking the user up until a time after the maximum number of minutes before the predetermined time, the system can project the circadian rhythm and help the user adjust the maximum number of minutes (and therefore the user's sleep schedule) to maximize sleep efficiency and quality. For instance, if the user knows that he or she has a sleep cycle of approximately 90 minutes and needs to be up by 7 AM, he or she could then chose to go to bed at approximately 11:30 PM or 1 AM to maximize the chance of his or her lightest stages of sleep occurring near the preferred wake up time.

With respect to the above description then, it is to be realized that material disclosed in the applicant's drawings and description may be modified in certain ways while still producing the same result claimed by the applicant. Such variations are deemed readily apparent and obvious to one skilled in the art, and all equivalent relationships to those illustrated in the drawings and equations and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. An apparatus for detecting Rapid Eye Movement (REM) in a sleeping mammal and awakening the mammal after the cessation of REM, the apparatus comprising:
   a. an alarm time setting means for setting a predetermined time;
   b. data collection means for collecting physiological data from the mammal over time;
   c. processing means for processing said physiological data in near real time to detect the occurrence of REM in said mammal; and
   d. a means for providing a stimulation signal for awakening said mammal after cessation of REM wherein said cessation of REM occurs within a maximum number of minutes before said predetermined time.

2. The apparatus of claim 1 wherein said maximum number of minutes is between 60 and 120.

3. The apparatus of claim 2 wherein said physiological data comprises an amount of eye movement over time.

4. The apparatus of claim 3 wherein said stimulation signal comprises auditory stimulation.

5. The apparatus of claim 3 wherein said processing means compares an amount of eye movement during a second time interval relative to an amount of eye movement during a first time interval.

6. The apparatus of claim 3 wherein said physiological data further comprises the body temperature of said mammal, wherein said processing means further comprises detecting the nadir of said temperature with respect to time, and wherein said stimulation signal is provided not before said nadir.

7. The apparatus of claim 6 wherein said stimulation signal comprises photic stimulation.

8. The apparatus of claim 7 wherein said photic stimulation is a light source having a wavelength of between 420-500 nanometers and wherein said light source increases in illumination from a value greater than 0 LUX to a value of not more than 10,000 LUX.

9. The apparatus of claim 7 further comprising a means for adjusting the ambient lighting of a room.

10. The apparatus of claim 9 wherein said photic stimulation is delivered by said ambient lighting.

11. A method of detecting Rapid Eye Movement (REM) sleep in a mammal and awakening the mammal after the cessation of REM sleep, the method comprising the steps of:
    a. setting a predetermined time;
    b. collecting physiological data from the mammal over time;
    c. processing said physiological data in near real time to detect the occurrence of REM in said mammal; and
    d. providing a stimulation signal for awakening said mammal after cessation of REM wherein said cessation of REM occurs within a maximum number of minutes before said predetermined time.

12. The method according to claim 11 wherein said physiological data comprises an amount of eye movement over time, and wherein said processing step determines a relative amount of eye movement based on said physiological data during a second time interval compared to said physiological data during a first time interval, and wherein said relative amount of eye movement falls below a minimum predetermined threshold before said step of providing a stimulation signal.

13. The method according to claim 12 wherein said physiological data further comprises the body temperature of said mammal, wherein said processing means further comprises determining a nadir of said body temperature with respect to time and wherein said nadir occurs before said step of providing a stimulation signal.

14. The method according to claim 13 wherein said stimulation signal comprises photic stimulation.

15. An method of awakening a sleeping mammal, the method comprising the steps of:
    a. collecting physiological data from the mammal over time, the physiological data comprising an amount of eye movement over time and the mammal's body temperature;
    b. processing said physiological data in near real time to detect the cessation of Rapid Eye Movement (REM) in said mammal and for detecting the nadir of said body temperature with respect to time; and
    c. providing a stimulation signal for awakening said mammal after cessation of REM and not before said body temperature nadir.

16. The method according to claim 15, further comprising:
    a. setting a predetermined time; and
    b. wherein said collecting step occurs after a maximum number of minutes before said predetermined time.

17. The method according to claim 16 wherein said maximum number of minutes is between 60 and 120.

18. The method according to claim 17 wherein said processing means compares an amount of eye movement during a second time interval relative to an amount of eye movement during a first time interval.

19. The method according to claim 18 wherein said stimulation signal comprises a photic stimulation having a wavelength of between 420-500 nanometers and wherein said light source increases in illumination from a value greater than 0 LUX to a value of not more than 10,000 LUX.

20. The apparatus of claim 19 further comprising a means for adjusting the ambient lighting of a room and wherein said photic stimulation is delivered by said ambient lighting.

* * * * *